United States Patent [19]

Beller et al.

[11] Patent Number: 5,650,537
[45] Date of Patent: Jul. 22, 1997

[54] PROCESS FOR THE PREPARATION OF N-ACYL-α-AMINO ACID DERIVATIVES

[75] Inventors: Matthias Beller, Niedernhausen; Hartmut Fischer, Hofheim; Thomas Gerdau, Eppstein; Peter Gross, Kelsterbach, all of Germany

[73] Assignee: Hoechst AG, Frankfurt am Main, Germany

[21] Appl. No.: 433,011

[22] Filed: May 2, 1995

[30] Foreign Application Priority Data

May 2, 1994 [DE] Germany .................. 44 15 312.0

[51] Int. Cl.$^6$ .................................. C07C 51/12
[52] U.S. Cl. .................. 562/519; 562/518; 562/517; 562/406
[58] Field of Search ................ 562/519, 518, 562/517, 406

[56] References Cited

U.S. PATENT DOCUMENTS 4,891,442  1/1990  Lin et al. ................ 562/450
4,918,222  4/1990  Lin et al. ................ 562/518

FOREIGN PATENT DOCUMENTS 862365  3/1941  France .
849554  9/1952  Germany .
2252770  8/1992  United Kingdom .

OTHER PUBLICATIONS

European Patent Search Report 95106329.6, Jun. 21, 1995.

C. Ferri, "Reaktionen der Organischen Synthese", 1978, Georg Thieme Verlag, Seite 293.

*Primary Examiner*—Porfirio Nazario-Gonzalez
*Assistant Examiner*—Rosalynd A. Williams
*Attorney, Agent, or Firm*—Connolly & Hutz

[57] ABSTRACT

A process for the preparation of N-acylglycine derivatives of the formula (I)

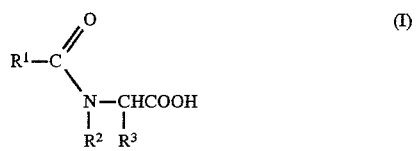

which comprises reacting a carboxylic acid amide with an aldehyde in the presence of a solvent and an acid to give an acylaminomethylol and then carbonylating the acylaminomethylol in the presence of a cobalt carbonyl catalyst.

31 Claims, No Drawings

PROCESS FOR THE PREPARATION OF N-ACYL-α-AMINO ACID DERIVATIVES

The present invention relates to a novel improved process for the preparation of N-acyl-α-amino acid derivatives, in particular N-acylsarcosines, by reaction of carboxylic acid amides with aldehydes and CO under acid catalysis by cobalt carbonyl compounds.

N-acyl-α-amino acid derivatives, in particular the N-acylsarcosines, are of industrial importance as a constituent of surfactants, soaps and emulsifiers.

The process currently used in the art for synthesis of such compounds comprises reacting fatty acid chlorides with the sodium salt of glycine or of sarcosine in a conventional Schotten-Baumann reaction. The salt is thereby automatically obtained and the use of chlorinating agents, such as phosgene or phosphoric trichloride, for preparation of the fatty acid chlorides are very disadvantageous from ecological aspects (J. Am. Chem. Soc. 78, 172, (1956)).

An ecologically improved process comprises reaction of fatty acid amides, which are accessible by aminolysis directly from naturally occurring fatty acids or fats, with formaldehyde and CO in the presence of a catalyst. This reaction, which is called amidocarbonylation, was first described by Wakamatsu in Chem. Commun. 1971, 1540 and in DE 2,115,985. According to these references, however, N-acetylglycine was obtained in a yield of only 26% from acetamide, paraformaldehyde and CO.

Other variants are described, for example, in EP 170,830 and EP 197,659. Amidocarbonylation of paraformaldehyde with acetamide to give acetylglycine is described here, promoters, such as nitriles, sulfoxides or phosphanes, being said to increase the selectivities and to improve recycling of the catalyst. However, even under optimized conditions, N-acetylglycine is obtained in a yield of only 70% in the best case.

It is also described in the literature that amides alkylated on the N atom give significantly poorer yields of N-alkylacylamino acids than comparable primary amides (P. Magnus, M. Slater, Tetrahedron Lett. 1987, 28, 2829).

J. Org. Chem. 147, 99 (1991) describes the preparation of N-acylsarcosine by carbonylation of N-methyllaurylamide under a CO+H$_2$ (3:1) pressure of more than 200 bar. In this process, the desired product is obtained only in a highly contaminated form.

GB 2 252 770 describes a one-stage synthesis of N-acylamino acids by reaction of a carboxylic acid amide with an aldehyde and CO in the presence of a metal catalyst and an acid as cocatalyst.

In this process, the carboxylic acid amide is employed in a very high excess, based on the aldehyde (1.78 to 1.0), so that this process gives only moderate yields based on the acetamide employed. Furthermore, the product is thereby contaminated with at least 80% of starting material, which renders the process unusable for industrial application.

All the processes described proceed with only inadequate conversions and selectivities, give contaminated products or require very high CO pressures.

DE-A-364 204 describes only a process for the preparation of N-acylglycines starting from N-hydroxymethylamides with carbon monoxide and hydrogen in the presence of a cobalt carbonyl compound in water or an inert water-containing solvent as the reaction medium.

The reaction in water or in solvents of high water content is a disadvantage of this process.

There was therefore a great need for a process which renders N-acyl-α-amino acid derivatives, in particular N-acylsarcosines, accessible in a high yield and purity in a manner which can easily be realized industrially.

This object is achieved by a process for the preparation of acylglycine derivatives of the formula (I)

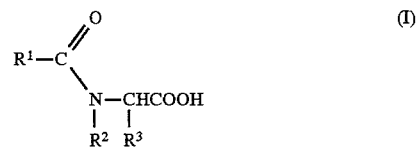

in which

R$^1$ is hydrogen, a saturated, straight-chain, branched or cyclic (C$_1$–C$_{26}$)alkyl radical, a mono- or polyunsaturated, straight-chain, branched or cyclic (C$_2$–C$_{24}$)alkenyl radical, a (C$_6$–C$_{18}$)aryl radical, a (C$_1$–C$_{10}$)alkyl-(C$_6$–C$_{18}$)aryl radical or an optionally polyunsaturated (C$_2$–C$_{10}$)alkenyl-(C$_6$–C$_{18}$)aryl radical, R$^2$ is hydrogen, a saturated, straight-chain, branched or cyclic (C$_1$–C$_{26}$)alkyl radical, a mono- or polyunsaturated, straight-chain, branched or cyclic (C$_2$–C$_{23}$) alkenyl radical, a (C$_6$–C$_{18}$) aryl radical, a (C$_1$–C$_{10}$) alkyl-(C$_6$–C$_{18}$) aryl radical or an optionally polyunsaturated (C$_2$–C$_{10}$) alkenyl- (C$^6$–C$_{18}$) aryl radical and R$^3$ is hydrogen, a saturated, straight-chain, branched or cyclic (C$_1$–C$_{10}$)alkyl radical, a mono- or polyunsaturated, straight-chain, branched or cyclic (C$_2$–C$_{10}$)alkenyl radical, a (C$_6$–C$_{18}$) aryl radical, a (C$_1$–C$_{10}$)alkyl-(C$_6$–C$_{18}$) aryl radical or an optionally polyunsaturated (C$_2$–C$_{10}$)alkenyl-(C$_2$–C$_{10}$) aryl radical, which comprises reacting a carboxylic acid amide of the formula (II)

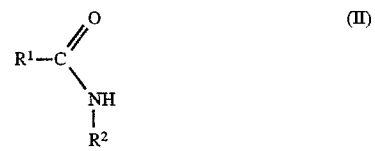

in which R$^1$ and R$^2$ have the abovementioned meaning, with an aldehyde of the formula R$^3$—CHO in the presence of a solvent and an acid to give an acylaminomethylol of the formula (III)

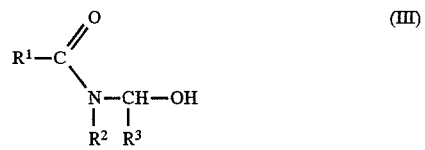

and then carbonylating this, after addition of a cobalt carbonyl catalyst and an acid as a cocatalyst, at a temperature of 20° to 150° C. under a CO pressure of 1 to 150 bar.

The radicals preferably have the following meanings:

R$^1$ is a saturated, straight-chain or branched (C$_8$–C$_{24}$) alkyl radical, in particular a (C$_{10}$–C$_{18}$)alkyl radical, or a mono- or- polyunsaturated, straight-chain or branched (C$_8$–C$_{24}$)alkenyl radical, in particular a (C$_{10}$–C$_{18}$)alkenyl radical, R$^2$ is hydrogen, a saturated, straight-chain or branched (C$_1$–C$_8$)alkyl radical, in particular a (C$_1$–C$_4$)alkyl radical, or a mono- or polyunsaturated, straight-chain or branched (C$_2$–C$_8$)alkenyl radical, and R3 is hydrogen, a saturated, straight-chain or branched (C$_1$–C$_6$)alkyl radical or a mono- or polyunsaturated, straight-chain or branched (C$_2$–C$_6$)alkenyl radical.

The radicals $R^1$, $R^2$ and $R^3$ can be optionally substituted.

Suitable substituents are the hydroxyl group, ($C_1$–$C_{10}$) alkoxy radicals and halogen atoms.

Suitable amides are, for example, formamide, acetamide, N-methylacetamide, propionamide, butyramide, acrylamide, N-methylformamide, N-methylbenzamide, benzamide and crotonamide.

Amides which are particularly suitable starting substances for the process according to the invention are amides and N-alkylamides, in particular N-methylamides, of straight-chain or branched, saturated or unsaturated carboxylic acids having 8 to 24 carbon atoms. Amides which may be mentioned specifically are:

octanoic acid amide, 2-ethylhexanoic acid amide, decanoic acid amide, lauric acid amide, palmitic acid amide, stearic acid amide, oleic acid amide, linoleic acid amide, linolenic acid amide, gadoleic acid amide and nervonic acid amide.

Particularly preferred amides are the N-methylamides of naturally occurring fatty acids, such as lauric acid, palmitic acid, stearic acid and oleic acid.

The amides of the formula (II) can be employed as pure substances or as mixtures. Suitable mixtures are the naturally occurring fats, for example coconut, babassu, palm kernel, palm, olive, castor, groundnut, rape seed, bovine, porcine and whale fat or oil (for the composition of these fats, cf. Fieser and Fieser, Organische Chemie (Organic Chemistry), Verlag Chemie 1972, page 1208).

Suitable aldehydes are, for example, formaldehyde, acetaldehyde, propionaldehyde, butyraldehyde, isobutyraldehyde, furfural, crotonaldehyde, acrolein, benzaldehyde, phenylacetaldehyde, 2,4-dihydroxyphenylacetaldehyde and α-acetoxypropionaldehyde. Substances which can form an aldehyde under the reaction conditions mentioned are also suitable, for example aldehyde oligomers, such as paraformaldehyde and paraldehyde. In many cases, it has proven suitable to employ formaldehyde in the form of paraformaldehyde.

The process according to the invention is carried out in two stages. In the first stage, the acylaminomethylol of the formula (III) is first formed from the aldehyde and the carboxylic acid amide, and is reacted in the second step with CO to give the end product. This two-stage procedure surprisingly allows a significant increase in conversion and selectivity in each stage, so that conversions of 100% of the carboxylic acid amide at selectivities of 98% for the N-acyl-α-amino acid derivative are achieved for the overall process, i.e. the yields of target product are also 98%.

A particularly favorable feature of the process according to the invention is that equimolar amounts of aldehyde already give high yields, and products which are not contaminated by aldehyde can thus be obtained. However, it is also possible to use excesses of aldehyde.

It has proved advantageous to employ 70 to 200 mol %, in particular 100 to 140 mol %, preferably 100 to 120 mol %, of aldehyde, based on the carboxylic acid amide.

The addition of the aldehyde to the carboxylic acid amide in the presence of an acid is carried out by heating in solution. In addition to organic acids, such as toluenesulfonic acid, hexafluoropropanesulfonic acid or trichloroacetic acid, and inorganic acids, such as sulfuric acid and phosphoric acid, ion exchanger resins can also be used as the acids.

Sulfuric acid is particularly suitable. The acid introduced into the reaction system can remain in the solution of the acyl-aminomethylol formed without thereby interfering with the subsequent carbonylation.

It has proved suitable in many cases to use acid concentrations of 0.2 to 5 mol %, in particular 0.5 to 4 mol %, preferably 1.0 to 2.5 mol %, based on the amide.

The reaction is expediently carried out in a polaraprotic solvent, such as, for example, tetrahydrofuran, glycol dimethyl ether, methyl t-butyl ether, diglycol dimethyl ether, dimethylformamide, dimethylacetamide or acetonitrile. Tetrahydrofuran, glycol dimethyl ether (glyme) and methyl t-butyl ether have proven particularly suitable. In the first stage, the carboxylic acid amide is reacted with the aldehyde in a stirred reactor under normal pressure. This reaction proceeds at 65° to 120° C. in the course of 10 to 60 minutes.

The amount of water present or which forms in the reaction batch must be kept as low as possible when carrying out the process according to the invention. Amounts of water up to 2% by weight, usually between 0.1 and 1% by weight, based on the reaction batch, are aimed for here. For this reason, it is preferable to employ anhydrous solvents. The use of so-called industrial solvents, which must meet the above requirements in respect of water content, is conceivable.

Clear solutions are then obtained, from which no solid crystallizes out even during prolonged standing (several days) at room temperature. For reaction procedure reasons, these solutions are employed for the carbonylation immediately after their preparation. Surprisingly, the resulting solutions are relatively stable, so that further processing can also be carried out after a certain storage time.

It is an important industrial advantage of the process that these solutions can be fed continuously to the carbonylation reactor via a pressurized metering pump, which means that the exothermic reaction can easily be controlled.

The carbonylation of the intermediate product of the formula (III) to give the end product of the formula (I) is carried out under 1 to 150 bar of carbon monoxide in a suitable reactor at temperatures of 20° to 150° C., in particular at 25° to 100° C., preferably at 30° to 70° C., under catalysis by cobalt carbonyl compounds. Carbon monoxide is expediently used as the pure gas, because the residual gas can then easily be recycled. The carbon monoxide employed can also contain a limited amount of hydrogen. Even if the carbon monoxide employed is contaminated with other gases, for example nitrogen, methane or carbon dioxide, which water gas usually contains, this has no adverse influence on the reaction. The pressure to be applied is at least 1 bar and must not exceed 100 bar. Given a suitable design of the reactor for effective introduction of gas into the solution, for example in a stirred reactor with a gassing stirrer or in a bubble column, the CO pressure can be reduced to less than 50 bar without problems. The process is therefore preferably carried out under a CO pressure of 1 to 50, particularly preferably 3 to 20 bar. CO-containing gas mixtures, for example synthesis gas CO+$H_2$ in the ratio 1:1, can also be employed. However, hydrogen is then concentrated in the residual gas, which complicates the circulatory procedure and increases the overall pressure of the reaction system.

The carbonylation is catalyzed by cobalt carbonyl. This can be added to the solutions of the methylol (III) as solid $Co_2(CO)_8$, dissolved and then introduced into the carbonylation reactor. However, the cobalt carbonyl can also be formed in a large amount in reserve in a separate pressurized reactor from a suitable cobalt(II) compound, such as, for example, cobalt(II) acetate, basic cobalt(II) carbonate or cobalt(II) ethylhexanoate, and CO, if appropriate with addition of $H_2$, in the same solvent as used for the methylol stage. A portion of this cobalt carbonyl solution is then added to the solution of the methylol III in the carbonylation reactor.

Preparation and keeping the $Co_2(CO)_8$ in solution in reserve has the advantage that the air-sensitive toxic substance does not have to be handled as a solid; the solutions can be stabilized by covering with a layer of CO. The amount of $Co_2(CO)_8$ added is chosen such that the reaction mixture comprises 0.1 to 5.0, preferably 0.6 to 2.0 mol % of Co, based on the carboxylic acid amide employed in stage 1. With the preferred catalyst concentration, the reaction starts at about 20° C., which can be seen from the uptake of CO. At a reaction temperature of 70° C. the reaction becomes so rapid that space/time yields of 300 g/l. h are achieved and exceeded. Sufficiently intensive introduction of gas into the solution should be ensured during the carbonylation in order to achieve a quantitative conversion.

After the reaction has subsided, which takes 0.5 to 2.0 h, depending on the CO pressure applied, the mixture is cooled and the excess gas is released. A clear, yellow- to brown-colored solution is removed from the reactor, and the homogeneously dissolved catalyst must first be removed from this. This is carried out in the customary manner by destroying the cobalt carbonyl compounds oxidatively by blowing in air and precipitating the divalent cobalt thereby formed as a sparingly soluble salt, for example oxalate, phosphate, sulfate or carbonate. This salt is filtered off. The resulting solution is at most pale yellow in color and contains the target product in a yield of 98%. Isolation and purification proceed easily, so that only minimum losses in yield occur during this operation. The solvent is separated off by distillation in a thin film evaporator; the distillate can be recycled into the process without limitation. The concentrate which drains down, comprising molten crude product, is introduced into hot water, dispersed thoroughly and crystallized by cooling. A white, water-moist product is isolated by filtration and is immediately suitable for most applications. Careful determination of the water content, together with HPLC analyses of both the moist and the dry product, demonstrate that the yields of target product are 94 to 98% of theory, based on the particular carboxylic acid amide employed.

The process according to the invention gives N-acyl-α-amino acid derivatives, in particular N-acylglycines and N-acylsarcosines, in a very good purity in practically quantitative yield, without by-products being obtained or expensive working up or afterpurification being necessary.

The process according to the invention is advantageously suitable for the preparation of N-acylsarcosines based on N-acylamides of long-chain saturated or unsaturated fatty acids.

The following examples are intended to illustrate the process, without limiting it.

EXAMPLE 1

Preparation of lauroylsarcosine 213 g (1 mol) of lauric acid N-methylamide and 34 g of paraformaldehyde (95% pure $\hat{=}$ 1.08 mol) are suspended in 350 ml of dimethoxyethane (glyme), and 2 g (0.02 mol) of $H_2SO_4$ are added.

1) This mixture is heated to the boiling point (boiling point=84°), while stirring, and kept at this temperature for 5 to 10 minutes. During this procedure, the solids largely dissolve. The mixture is cooled to about 60° C. and the still hot, slightly cloudy solution is filtered.

A clear solution which can be stored at room temperature in closed vessels without decomposition is obtained. In open vessels, however, the solution slowly loses gaseous formaldehyde and lauric acid N-methylamide starts to crystallize out after a few days.

2) 2.02 g (5.85 mmol) of $Co_2(CO)_8$ (corresponding to 11.7 mmol of CO or 1.17%) are added to the solution of the addition product of lauric acid N-methylamide and formaldehyde and the mixture is introduced into a 1 l autoclave. 20 bar of CO are forced in and the mixture is heated to 70° C. The start of the reaction can be detected from the falling pressure; the CO is then topped up in order to maintain the pressure in the reactor. The majority of the gas is taken up within 30 to 60 minutes; to bring the conversion reliably to 100%, the mixture is subsequently stirred for 1 h. The reactor is cooled, the excess gas is released and the clear yellow product solution is removed.

2 g (22 mmol) of oxalic acid are added to the solution containing cobalt carbonyl, and air is passed in, while stirring thoroughly. After 1 h, precipitation of the cobalt oxalate is complete. This is filtered off. The glyme is then removed from the solution in a thin film evaporator (oil temperature 140° to 150° C.). The molten crude product flowing off as the concentrate is dispersed (emulsified) in 1 l of hot water at 60°–80° C. in order to remove residues of solvent, formaldehyde and the acid from reaction stage 1. The emulsion is cooled slowly, while stirring, and at 15° to 5° C. the lauroylsarcosine crystallizes. It is filtered off with suction, rinsed with water and pressed dry.

Yield of water-moist product: 451.7 g

Determination of the moisture content showed a water content of 41.2% =186 g of $H_2O$.

Yield of lauroylsarcosine =265.6$\hat{=}$98% of theory.

The dry product has a melting point =49° to 50° C.

HPLC and H-NMR confirm a high purity of >99.7%.

EXAMPLES 2 to 9

These examples were carried out analogously to Example 1 with different starting substances, sometimes on a reduced scale. The amounts of substances and results are summarized in Table 1. The 0.2 mol batches were carried out in a 200 ml autoclave, the CO pressure being increased to 50 bar.

TABLE 1

| Example | Carboxylic acid amide | Paraformaldehyde 95% pure | Dimethoxyethane | Acid | $Co_2(CO)_8$ | Yield |
|---|---|---|---|---|---|---|
| 2 | Lauric acid amide 199 g | 36 g 1.14 mol | 350 ml | $H_2SO_4$ 2 g | 1.85 g | 247 g $\hat{=}$ 96.1% lauroylglycine |
| 3 | Stearic acid N-methylamide 297 g | 34 g 1.08 mol | 350 ml | $H_2SO_4$ 2 g | 1.73 g | 346 g $\hat{=}$ 97.5% stearoylsarcosine |
| 4 | Stearic acid amide 57 g | 7.4 g 0.23 mol | 70 ml | $H_2SO_4$ 0.4 g | 0.31 g | 64.9 g $\hat{=}$ 95.2% stearoylglycine |
| 5 | Decanoic acid amide 34 g | 7.5 g 0.23 mol | 70 ml | $H_2SO_4$ 0.4 g | 0.35 g | 43.3 g $\hat{=}$ 94.5% decanoylglycine |
| 6 | Lauric acid methylamide 42.6 g | 6.6 g 0.2 mol | 60 ml | hexafluoropropanesulfonic acid 0.4 g | 0.20 g | 51.5 g $\hat{=}$ 95% lauroylsarcosine |

TABLE 1-continued

| Example | Carboxylic acid amide | Paraformaldehyde 95% pure | Dimethoxyethane | Acid | Co₂(CO)₈ | Yield |
|---|---|---|---|---|---|---|
| 7 | Oleic acid methylamide 148 g | 19 g 0.60 mol | 200 ml | $H_2SO_4$ 0.5 g | 1.97 g | 173 g ≙ 98% oleyl-sarcosine |
| 8 | Acetic acid tetradecanylamide 128 g | 19 g 0.60 mol | 275 ml | $H_2SO_4$ 0.5 g | 3.41 g | 131 g ≙ 84% N,N-acetyl-tetradecanyl-glycine |
| 9 | Lauric acid iso-butylamide 127.5 g | 17.5 g 0.55 mol | 200 ml | $H_2SO_4$ 0.5 g | 2.00 g | 145 g ≙ 93% N-Lauroyl-N-isobutyl-sarcosine |

EXAMPLE 10

Preparation of N-lauroyl-1-propyl-sarcosine 21.3 g (0.1 mol) of lauric acid N-methylamide and 8.8 g of butyraldehyde (0.12 mol) are suspended in 35 ml of ethyl acetate, and 0.3 g (1.3 mmol) of hexafluoropropanesulfonic acid is added.

1) This mixture is heated to 95° C. in an autoclave, while stirring, and is kept at this temperature for 5 to 10 minutes. It is then allowed to cool to room temperature.

2) 0.35 g (1.02 mmol) of $Co_2(CO)_8$ is added to the solution of the addition product of lauric acid N-methylamide and butyraldehyde. 50 bar of CO are forced in and the mixture is heated to 70° C. The start of the reaction can be detected by the falling pressure; the CO is then topped up in order to maintain the pressure in the reactor. The majority of the gas is taken up within 60 minutes; to bring the conversion reliably to 100%, the mixture is subsequently stirred for 2 hours. The reactor is cooled, the excess gas is released and the yellow clear product solution is removed.

0.5 g (5.5 mmol) of oxalic acid is added to the solution containing cobalt carbonyl, and air is passed in, while stirring thoroughly. After 1 hour, precipitation of the cobalt oxalate is complete. This is filtered off. The ethyl acetate is then removed from the solution in a thin-film evaporator (oil temperature 140° to 150° C.). The molten crude product flowing off as the concentrate is dispersed (emulsified) in 200 ml of hot water at 60°–80° C. in order to remove residues of solvent, formaldehyde and the acid from reaction stage 1. The emulsion is cooled slowly, while stirring, and N-lauroyl-1-propyl-sarcosine crystallizes at 15° to 5° C. It is filtered off with suction, rinsed with water and pressed dry. yield of N-lauroyl-1-propyl-sarcosine =27.0 g ≙86% of theory The dry product has a melting point =50° to 51° C.

We claim:

1. A process for the preparation of an acylglycine derivature of the formula (I)

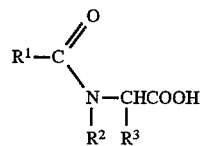

in which

R¹ is hydrogen, a saturated, straight-chain, branched or cyclic ($C_1$–$C_{26}$) alkyl radical, a mono- or polyunsaturated, straight-chain, branched or cyclic ($C_2$–$C_{24}$) alkenyl radical, a ($C_6$–$C_{18}$) aryl radical, a ($C_1$–$C_{10}$) alkyl- ($C_6$–$C_{18}$) aryl radical or an optionally polyunsaturated ($C_2$–$C_{10}$) alkenyl- ($C_6$–$C_{18}$) aryl radical, R² is hydrogen, a saturated, straight-chain, branched or cyclic ($C_1$–$C_{26}$) alkyl radical, a mono- or polyunsaturated, straight-chain, branched or cyclic $C_2$–$C_{23}$) alkenyl radical, a ($C_6$–$C_{18}$) aryl radical, a ($C_1$–$C_{10}$) alkyl- ($C_6$–$C_{18}$)aryl radical or an optionally polyunsaturated ($C_2$–$C_{10}$) alkenyl- ($C_6$–$C_{18}$) aryl radical and R³ is hydrogen, a saturated, straight-chain, branched or cyclic ($C_1$–$C_{10}$) alkyl radical, a mono- or polyunsaturated, straight-chain, branched or cyclic ($C_2$–$C_{10}$) alkenyl radical, a ($C_6$–$C_{18}$)aryl radical, a ($C_1$–$C_{10}$) alkyl- ($C_6$–$C_{18}$) aryl radical or an optionally polyunsaturated ($C_2$–$C_{10}$) alkenyl- ($C_6$–$C_{18}$) aryl radical, which comprises reacting a carboxylic acid amide of the formula (II)

in which R¹ and R² have the abovementioned meaning, with an aldehyde of the formula R³CHO in the presence of a solvent and an acid to give an acylaminomethylol of the formula (III)

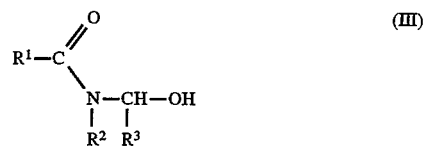

and then carbonylating this, after addition of a cobalt carbonyl catalyst, at a temperature of 20° to 150° C. under a CO pressure of 1 to 150 bar, wherein the aldehyde is employed in an amount of 70 to 200 mol % based on the carboxylic acid amide.

2. The process as claimed in claim 1, wherein the amide of a naturally occurring fatty acid is employed as the compound of the formula II.

3. The process as claimed in claim 1, wherein R² is hydrogen or ($C_1$–$C_4$) alkyl.

4. The process as claimed in claim 1, wherein octanoic acid amide, 2-ethylhexanoic acid amide, decanoic acid amide, lauric acid amide, palmitic acid amide, stearic acid amide, lauric acid N-methylamide, palmitic acid N-methylamide, stearic acid N-methylamide or oleic acid N-methylamide is employed as the compound of the formula (II).

5. The process as claimed in claim 1, wherein the compound of the formula (II) is employed as a mixture such as is obtainable from naturally occurring fats.

6. The process as claimed in claim 1, wherein formaldehyde is employed in the form of paraformaldehyde.

7. The process as claimed in claim 1, wherein an ion exchanger resin or an organic or inorganic acid is employed as the acid.

8. The process as claimed in claim 1, wherein the acid is employed in an amount of 0.2 to 5 mol % based on the amide.

9. The process as claimed in claim 1, wherein a dipolar aprotic solvent is employed as solvent.

10. The process as claimed in claim 1, wherein the reaction of the amide with the aldehyde is carried out at a temperature of 65° to 120° C.

11. The process as claimed in claim 1, wherein the carbonylation is carried out at a temperature of 25° to 100° C.

12. The process as claimed in claim 1, wherein the carbonylation is carried out under a CO pressure of 1 to 50 bar.

13. The process as claimed in claim 1, wherein pure carbon monoxide is employed for the carbonylation.

14. The process as claimed in claim 1, wherein a mixture of carbon monoxide and hydrogen is employed for the carbonylation.

15. The process as claimed in claim 1, wherein $Co_2(CO)_8$ is employed as cobalt carbonyl.

16. The process as claimed in claim 1, wherein the cobalt carbonyl is employed in an amount of 0.1 to 5.0 mol % of cobalt, based on the carboxylic acid amide.

17. The process as claimed in claim 1, wherein $R^2$ is methyl.

18. The process as claimed in claim 1, wherein the aldehyde is employed in an amount of from 100 to 140 mol % based on the carboxylic acid amide.

19. The process as claimed in claim 1, wherein the aldehyde is employed in an amount of from 100 to 120 mol % based on the carboxylic acid amide.

20. The process as claimed in claim 1, wherein toluene sulfonic acid, hexafluoropropane sulfonic acid, trichloroacetic acid, sulfuric acid or phosphoric acid are employed as the acid.

21. The process as claimed in claim 1, wherein sulfuric acid is employed as the acid.

22. The process as claimed in claim 1, wherein the acid is employed in an amount of 0.5 to 4 mol %, based on the amide.

23. The process as claimed in claim 1, wherein the acid is employed in an amount of 1.0 to 2.5 mol % of the amide.

24. The process as claimed in claim 1, wherein the solvent is tetrahydrofuran, glycol dimethyl ether, diglycol dimethyl ether, dimethyl formamide, or dimethyl acetamide.

25. The process as claimed in claim 1, wherein the solvent is tetrahydrofuran, glycol dimethyl ether, or methyl t-butyl ether.

26. The process as claimed in claim 1, wherein the carbonylation is carried out at a temperature of from 30° to 70° C.

27. The process as claimed in claim 1, wherein the carbonylation is carried out under pressure of 3 to 20 bar.

28. The process as claimed in claim 1, wherein the colbalt carbonyl is employed in an amount of from 0.6 to 2.0 mol % of cobalt, based on the carboxylic acid amide.

29. A process for the preparation of an acylglycine derivative of the formula (I)

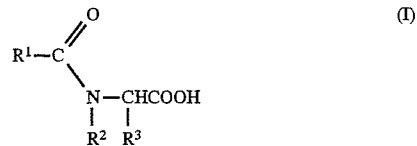

in which $R^1$ is hydrogen, a saturated, straight-chain, branched or cyclic ($C_1$–$C_{26}$) alkyl radical, a mono- or polyunsaturated, straight-chain, branched or cyclic ($C_2$–$C_{24}$) alkenyl radical, a ($C_6$–$C_{18}$) aryl radical, a ($C_1$–$C_{10}$) alkyl-($C_6$–$C_{18}$) aryl radical or an optionally polyunsaturated ($C_2$–$C_{10}$) alkenyl-($C_6$–$C_{18}$) aryl radical, $R^2$ is hydrogen, a saturated, straight-chain, branched or cyclic ($C_1$–$C_{26}$) alkyl radical, a mono- or polyunsaturated, straight-chain, branched or cyclic ($C_2$–$C_{23}$) alkenyl radical, a ($C_6$–$C_{18}$) aryl radical, a ($C_1$–$C_{10}$) alkyl-($C_6$–$C_{18}$) aryl radical or an optionally polyunsaturated ($C_2$–$C_{10}$) alkenyl-($C_6$–$C_{18}$) aryl radical and $R^3$ is hydrogen, a saturated, straight-chain, branched or cyclic ($C_1$–$C_{10}$) alkyl radical, a mono- or polyunsaturated, straight-chain, branched or cyclic ($C_2$–$C_{10}$) alkenyl radical, a ($C_6$–$C_{18}$) aryl radical, a ($C_1$–$C_{10}$) alkyl-($C_6$–$C_{18}$) aryl radical or an optionally polyunsaturated ($C_2$–$C_{10}$) alkenyl-($C_6$–$C_{18}$) aryl radical, which comprises reacting an amide of a naturally occurring fatty acid with an aldehyde of the formula $R^3CHO$ in the presence of a solvent and an acid to give an acylaminomethylol of the formula (III)

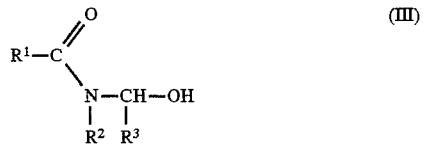

and then carbonylating this, after addition of a cobalt carbonyl catalyst, at a temperature of 20° to 150° C. under a CO pressure of 1 to 150 bar, wherein the aldehyde is employed in an amount of 70 to 200 mol % based on the amide of the naturally occurring fatty acid.

30. A process for the preparation of an acylglycine derivative of the formula (I)

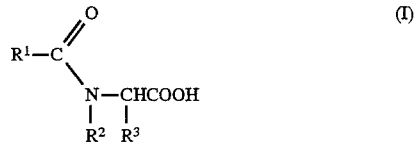

in which $R^1$ is hydrogen, a saturated, straight-chain, branched or cyclic ($C_1$–$C_{26}$) alkyl radical, a mono- or polyunsaturated, straight-chain, branched or cyclic ($C_2$–$C_{24}$) alkenyl radical, a ($C_6$–$C_{18}$) aryl radical, a ($C_1$–$C_{10}$) alkyl-($C_6$–$C_{18}$) aryl radical or an optionally polyunsaturated ($C_2$–$C_{10}$) alkenyl-($C_6$–$C_{18}$) aryl radical, $R^2$ is hydrogen, a saturated, straight-chain, branched or cyclic ($C_1$–$C_{26}$) alkyl radical, a mono-or polyunsaturated, straight-chain, branched or cyclic ($C_2$–$C_{23}$) alkenyl radical, a ($C_6$–$C_{18}$) aryl radical, a ($C_1$–$C_{10}$) alkyl-($C_6$–$C_{18}$) aryl radical or an optionally polyunsaturated ($C_2$–$C_{10}$) alkenyl-($C_6$–$C_{18}$) aryl radical and $R^3$ is hydrogen, a saturated, straight-chain, branched or cyclic $(C_1-C_{10})$ alkyl radical, a mono- or polyunsaturated, straight-chain, branched or cyclic $(C_2-C_{10})$ alkenyl radical, a $(C_6-C_{18})$ aryl radical, a $(C_1-C_{10})$ alkyl-$(C_6-C_{18})$ aryl radical or an optionally polyunsaturated $(C_2-C_{10})$ alkenyl-$(C_6-C_{18})$ aryl radical, which comprises reacting a carboxylic acid amide selected from the group consisting of octanoic acid amide, 2-ethylhexanoic acid amide, decanoic acid amide, lauric acid amide, palmitic acid amide, stearic acid amide, lauric acid N-methylamide, palmitic acid N-methylamide, stearic acid N-methylamide and oleic acid N-methylamide, with an aldehyde of the formula $R^3CHO$ in the presence of solvent and an acid to give an acylaminomethylol of the formula (III)

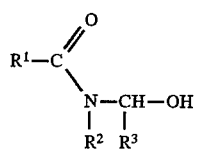

(III)

and then carbonylating this, after addition of a cobalt carbonyl catalyst, at a temperature of 20° to 150° C. under a CO pressure of 1 to 150 bar, wherein the aldehyde is employed in an amount of 70 mol % based on the carboxylic acid amide.

31. A process for the preparation of an acylglycine derivative of the formula (I)

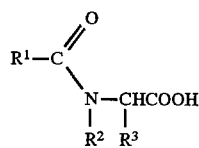

(I)

in which $R^1$ is hydrogen, a saturated, straight-chain, branched or cyclic $(C_1-C_{26})$ alkyl radical, a mono- or polyunsaturated, straight-chain, branched or cyclic $(C_2-C_{24})$ alkenyl radical, a $(C_6-C_{18})$ aryl radical, a $(C_1-C_{10})$ alkyl-$(C_6-C_{18})$ aryl radical or an optionally polyunsaturated $(C_2-C_{10})$ alkenyl-$(C_6-C_{18})$ aryl radical, $R^2$ is hydrogen, a saturated, straight-chain, branched or cyclic $(C_1-C_{26})$ alkyl radical, a mono- or polyunsaturated, straight-chain, branched or cyclic $(C_2-C_{23})$ alkenyl radical, a $(C_6-C_{18})$ aryl radical, a $(C_1-C_{10})$ alkyl-$(C_6-C_{18})$ aryl radical or an optionally polyunsaturated $(C_2-C_{10})$ alkenyl-$(C_6-C_{18})$ aryl radical and $R^3$ is hydrogen, a saturated, straight-chain, branched or cyclic $(C_1-C_{10})$ alkyl radical, a mono- or polyunsaturated, straight-chain, branched or cyclic $(C_2-C_{10})$ alkenyl radical, a $(C_6-C_{18})$ aryl radical, a $(C_1-C_{10})$ alkyl-$(C_6-C_{18})$ aryl radical or an optionally polyunsaturated $(C_2-C_{10})$ alkenyl-$(C_6-C_{18})$ aryl radical, which comprises reacting a carboxylic acid amide of the formula (II)

(II)

in which $R^1$ and $R^2$ have the above-mentioned meaning, with an aldehyde of the formula $R^3CHO$ in the presence of a solvent and sulfuric acid to give an acylaminomethylol of the formula (III)

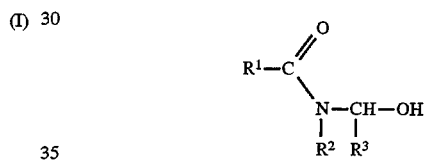

(III)

and then carbonylating this, after addition of a cobalt carbonyl catalyst, at a temperature of 20° to 150° under a CO pressure of 1 to 150 bar wherein the aldehyde is employed in an amount of 70 to 200 mol % based on the carboxylic acid amide.

* * * * *